United States Patent [19]

Dandeneau

[11] Patent Number: 4,888,146
[45] Date of Patent: Dec. 19, 1989

[54] METHOD AND APPARATUS OF FORMING EXTRUDED ARTICLE

[76] Inventor: James V. Dandeneau, 55 Tarkiln Rd., Harrisville, R.I. 02830

[21] Appl. No.: 196,016

[22] Filed: May 19, 1988

[51] Int. Cl.$^4$ ............................................. B29C 47/74
[52] U.S. Cl. ..................................... 264/171; 264/173; 264/DIG. 69; 425/131.1; 425/132; 425/192 R
[58] Field of Search ............... 264/171, 173, 167, 150, 264/DIG. 69; 425/131.1, 132, 192 R, 133.1, 133.5, 382.3, 382.4; 604/264, 280

[56] References Cited

U.S. PATENT DOCUMENTS

| | | | |
|---|---|---|---|
| 2,632,202 | 3/1953 | Haines | 264/245 |
| 3,345,444 | 10/1967 | Pratt | 264/167 |
| 3,743,457 | 7/1973 | Cini | 425/133.1 |
| 3,752,617 | 8/1973 | Burlis et al. | 425/131.1 |
| 4,185,951 | 1/1980 | Webermeier et al. | 425/382.4 |
| 4,276,250 | 6/1981 | Satchell et al. | 425/132 |
| 4,330,497 | 5/1982 | Agdanowski | 264/150 |
| 4,596,563 | 6/1986 | Pande | 264/173 |
| 4,636,346 | 1/1987 | Gold et al. | 264/150 |
| 4,761,129 | 8/1988 | Aste et al. | 425/133.1 |

FOREIGN PATENT DOCUMENTS

| | | | |
|---|---|---|---|
| 537801 | 3/1957 | Canada | 425/131.1 |
| 53-120773 | 10/1978 | Japan | 264/173 |
| 58-11118 | 1/1983 | Japan | 264/173 |
| 1392291 | 4/1975 | United Kingdom | 264/173 |

*Primary Examiner*—Jeffery Thurlow
*Attorney, Agent, or Firm*—Robert J. Doherty

[57] ABSTRACT

An article such as a length of plastic tubing is integrally formed by melt extrusion and having opposite ends which in turn are provided with different flexibilities. The apparatus and extrusion method by which such articles are forming in a running length includes a gear assembly rotatable between at least two alternate positions whereby two different but mixable resins are alternatively extruded as product.

15 Claims, 4 Drawing Sheets

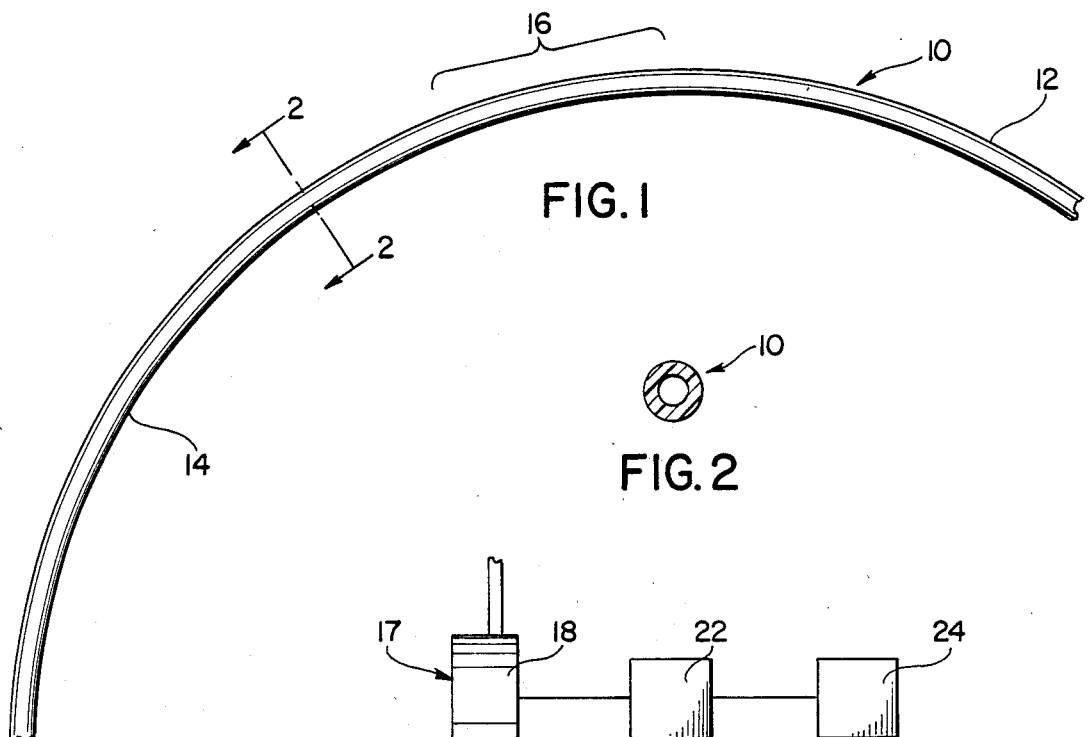
FIG. 1
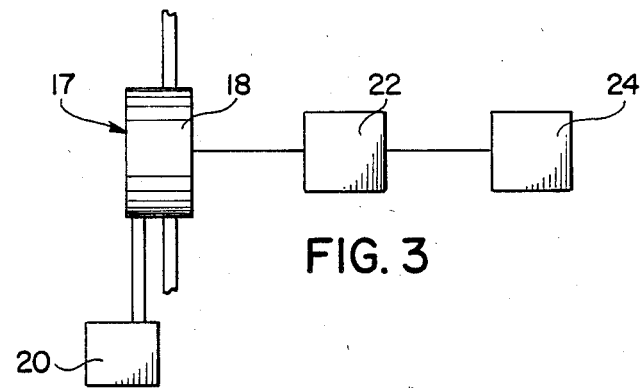
FIG. 2
FIG. 3
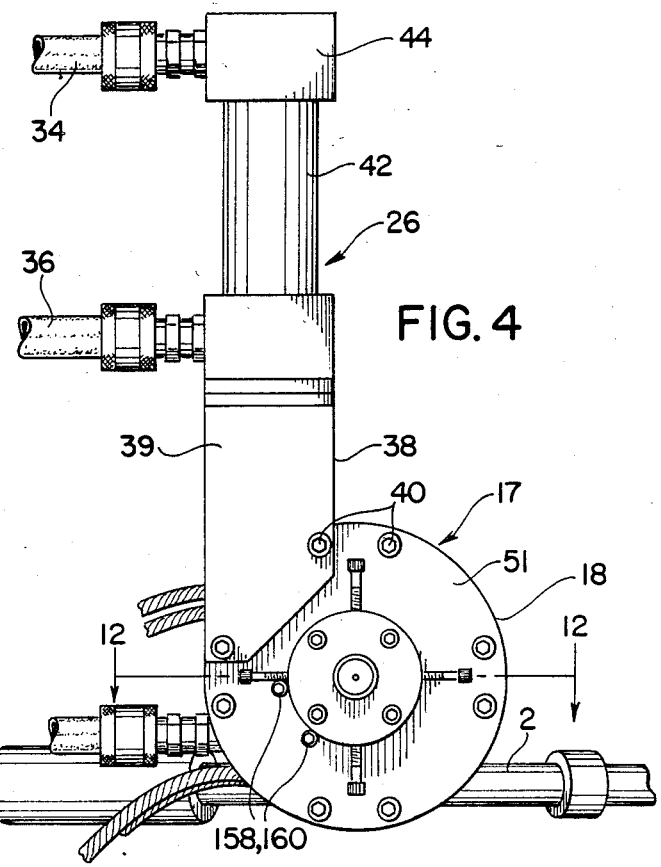
FIG. 4

METHOD AND APPARATUS OF FORMING EXTRUDED ARTICLE

BACKGROUND AND OBJECTS OF THE INVENTION

This invention relates to an article of extruded plastic wherein one end thereof has a varying physical characteristic from the other end thereof, e.g., varying flexibility, including the method and apparatus for producing such an article.

An example of an area where such an article might be used is the medical field such as a substitute for presently available catheter tubes. It is desirable in such catheter tubes that one end be relatively stiff while the other end by relatively flexible such that the more flexible lead end aids in insertion and is less traumatic once inserted into the body vessel by the doctor or medical technician. For this purpose, it is now known to join two hollow extruded plastic tubes of dissimilar flexibilities by a melt bonding technique, i.e., the butt ends of the tubes are heated to the softening point, and the adjacent areas fused to join their ends to form a continuous tube of dissimilar flexible ends. It is also known to adhesively connect the base ends of such tubes as by radio frequency bonding to form the desired result. However, such connections can and sometimes do fail under use such as upon being pressurized for injection (e.g., injection of contrast media); and, accordingly, a less labor intensive and more fail-safe article including such above-mentioned physical characteristics is needed.

Accordingly, the primary object of this invention is to supply such an article that is highly reliable yet can be produced at a reasonable cost.

Another and further object of the present invention is the provision of a method and apparatus for reasonably and assuredly forming such articles as indicated above.

These and other objects of the present invention are accomplished by the provision of a continually melt extruded length of article comprising first and second terminal end portions formed of compatible first and second melt mixable plastics and an intermediate connecting portion connecting joining said end portions wherein said first and second end portions have varying physical characteristics such as flexibility and said intermediate portion being a melt extrusion blending of said first and second plastics. The above article is formed in an unique melt extrusion process wherein two extruders are connected at a common head, and a gear assembly receives the output of such extruders such that the gear system may be driven between first and second positions in which similar, i.e., compatible, plastic resins from the extruders are alternately directed into an extrusion die such that a bridging section of mixed resins is formed as a connecting portion. The dwell period in which the dissimilar resins are mixed is of very short duration such that a fairly pronounced demarcation line is formed between the two end portions of the article length.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is an elevational view of a length of article formed in accordance with the present invention;

FIG. 2 is a sectional view taken along the line 2-2 of FIG. 1;

FIG. 3 is a schematic view showing the overall extrusion line for forming such articles;

FIG. 4 is a front elevational view showing the extruders, extrusion head assembly, and the control assembly;

DETAILED DESCRIPTION OF THE INVENTION

Figure 5:
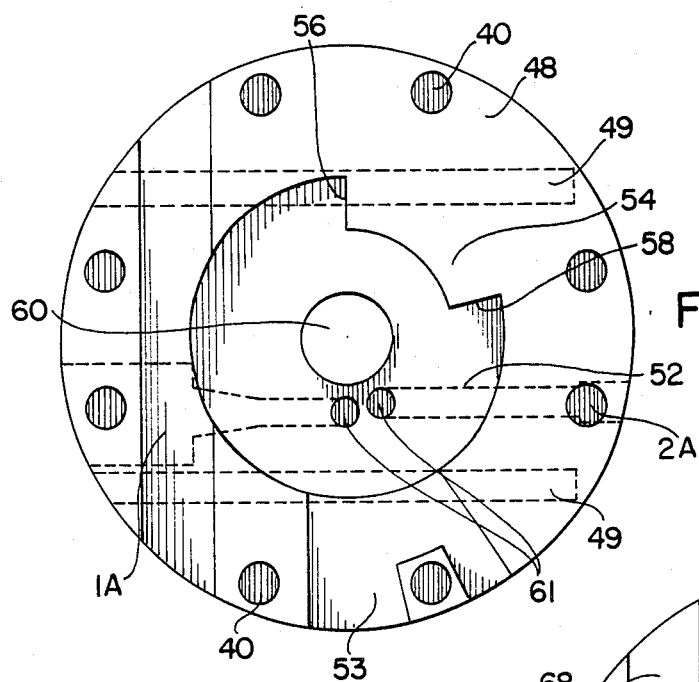
FIG. 5 is a front view of the base or rear section of the extrusion head.

Turning now to the drawings and particularly FIGS. 1 and 2 thereof, the novel construction of the article of the present invention is best shown. Therein a running length of article 10 is depicted. Such article, as best shown in FIG. 2, is of hollow tubular construction and may be adapted for medicinal purposes such as the flexible shaft portion of a catheter. Although the subject invention will be described with respect to such specialized medicinal use, it should be pointed out that other uses may indeed by placed upon such article, and it may be of a profiled configuration or even in the form of a coating upon an interior core instead of hollow. Generally for such specialized catheter uses, it is desirable to have the end to be inserted into a body vessel (artery, vein or other body passage) flexible and the other end stiff to aid in insertion.

Returning to the description, the article 10 includes first and second end portions 12 and 14 respectively. Although the entire article is preferably formed from similar or the same material having different physical characteristics, e.g. of differing flexibility, at its opposite ends 12 and 14, it is only necessary that the compositions forming the respective first and second ends 12 and 14 be compatible such that an intermediate connecting portion 16 be made up of differing quantities of each of the plastics forming the respective first and second ends 12 and 14. It is important, however, that the transition zone 16 be of relatively short length. For instance, with a 0.092 mil OD tubing with a 0.012 wall thickness formed of radiopaque plasticized nylon, it has been found desirable for the above-discussed medical application to have a transition zone 16 completed in a length of five inches. Other applications, however, may require shorter or longer lengths and such can be accomplished through programmed forming apparatus as will hereinafter be discussed.

Turning now to FIG. 3 of the drawings, the overall extrusion apparatus for carrying out the process of the present invention is depicted. Therein an extrusion head 18 is regulated by a control device 20 such that plastic material entering such extrusion from extruders 1 and 2 is progressively fed through an extrusion assembly 17 into a cooling trough or station 22 and then to a wind-up reel or station 24.

The extrusion assembly 17 is further shown in the remaining drawings including FIG. 4 wherein the relationship of a piston assembly 26 with the extrusion assembly 17 is best depicted. Therein the extrusion head 18, which in turn includes a gear or valve assembly 28 and a die assembly 30, is operatively associated with the piston assembly 26. The piston assembly 26 includes a hydraulically-operated piston 32 that is actuated back and forth between first and second positions by fluid power carried by the hydraulic hoses 34 and 36 and in turn controlled by the control programmer 20 as is conventional. The piston assembly 26 is further comprised of an elongated housing 38 including plate or plates 39 connected to the forward face of the extrusion head 18 with bolts 40. The cylinder 42 is held between upper and lower caps 44 in turn connected to the plate 39 such that the piston 32 reciprocated between opposed upper and lower positions and maintains one or the other of such positions for a length of time determined by the program such that a rack 46 connected thereto moves the gear assembly 28 between at least two operable positions as will hereinafter by more fully brought out.

Extruder 1 and extruder 2 shown best in Figs. 4 and 5 are connected to the base section or plate 48 of the head 18 which may in turn by heated by electric rods 49. The generally circular-shaped head 18 includes the base or rear section 48 and a forward section or plate 51 joined together with bolts 40. The base plate 48 in turn is provided with a central recess 52 of a partial circular configuration, that is, provided with a projecting inset 54, in turn forming shoulders or stop surfaces 56 and 58. Centrally of the recess 52 is an upstanding circular boss 60 preferably formed from a softer material such as brass than the tool or stainless steel normally used in forming the remaining portions of the extrusion assembly 17. Openings 61 and 62 connected respectively to passageways 1A and 2A respectively exit at the face of the recess 52 in a centrally offset but within a radial arc and positioned generally adjacent to each other. The recess 52 includes a cut-out section 53 which extends to the base plate 48 periphery for a purpose which will hereinafter be made clear.

Figure 6:
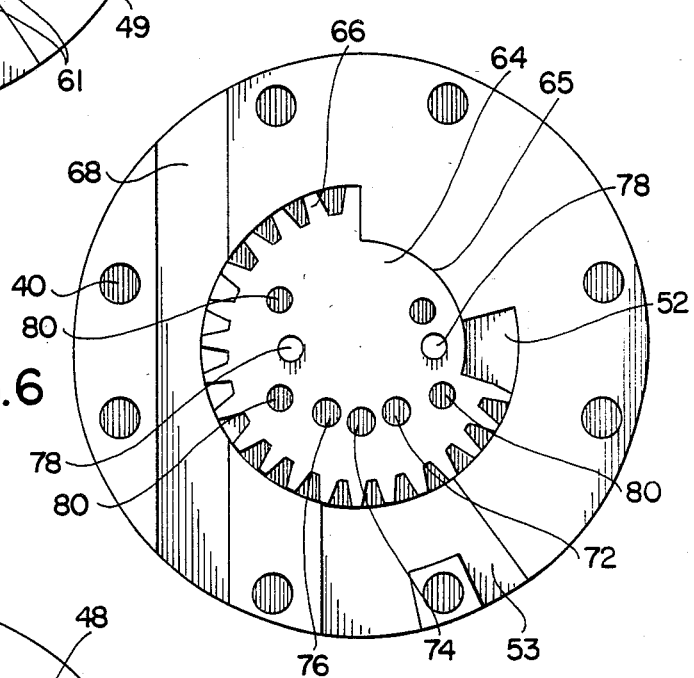
FIG. 6 is a view similar to FIG. 5 showing one portion of the gear assembly in position thereon.
Figure 7:
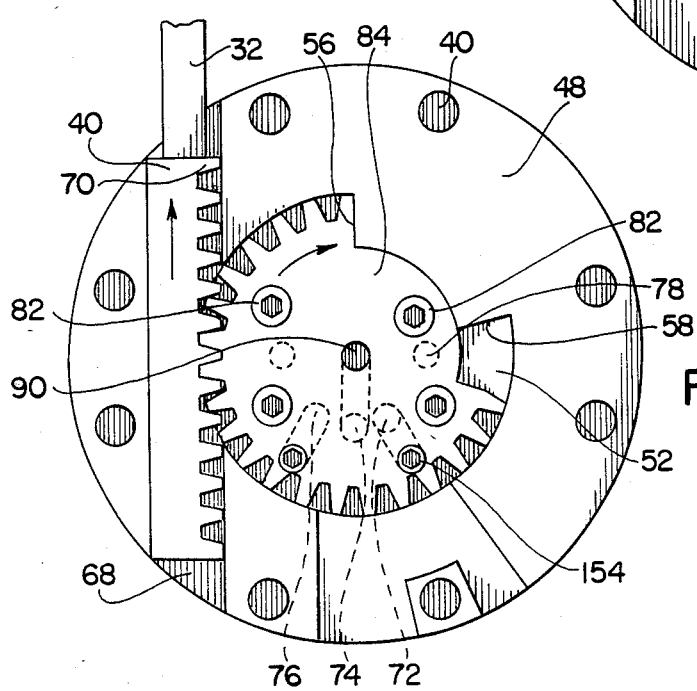
FIG. 7 is a view similar to FIG. 5 and 6 but showing the entire gear assembly in mounted and operable position vis-a-vis a slidable rack.
Figure 8:
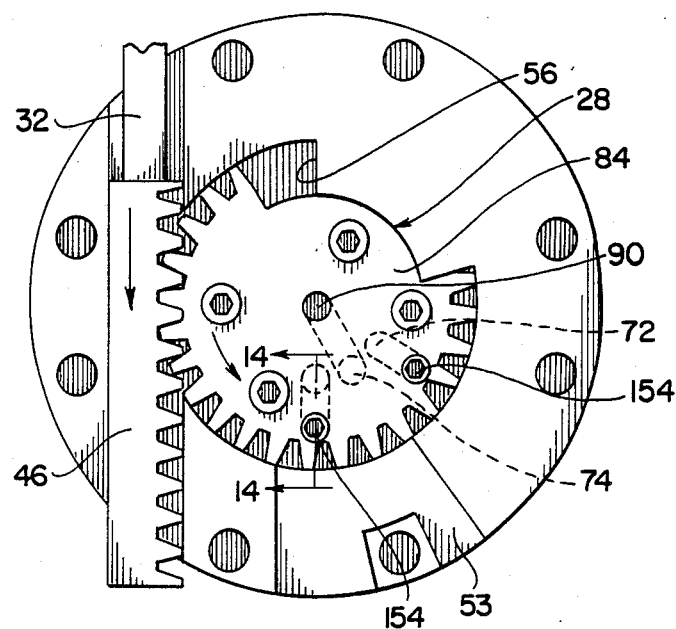
FIG. 8 is a front elevational view of the extrusion head and rack and gear assembly in an alternate position from that shown in FIG. 7.

A first element or gear 64 of the gear assembly 28 is positioned in the recess 52 and in turn includes a circular recess (not shown) for co-action with the brass boss 60 such that the gear 64 may be easily rotated within the limits provided by the stops 56 and 58. In that regard, it should be pointed out that the gear 64 is also of partial circular configuration but has an arcuate circumferential cut-out 65 of a slightly greater arcuate extent than that of the inset 54 and in this manner provides the ability of the gear to partially rotate between the two positions determined by contact with stops 56 and 58 by the gear. The gear 64 periphery includes teeth 66 adapted to partially extend into a vertical channel 68 formed in the base section 48 and in which the rack 46 is positioned. Such rack includes teeth 70 adapted to engage the teeth 66 such that the reciprocating piston movement 32 will move the gear 64 between a first position such as shown in FIGS. 6 and 7 and a second alternative position such as shown in FIG. 8.

The gear 64 is further provided with three centrally offset but arcuately aligned openings 72, 74, and 76. The alignment of the openings 72, 74, and 76 and the openings 61 and 62 is such that in the first position, as shown in FIGS. 6 and 7, two of the three gear 64 openings are aligned with both of the openings 61 and 62 but in the alternate positions, as shown in FIG. 8, two different openings of the three openings provided in the first gear 64 are aligned with the extrusion openings 61 and 62. The first gear is also provided with a pair of alignment pins 78 and four threaded openings 80 for receipt of bolts 82 such that a second gear similarly shaped to the first gear 64 may be aligned and bolted together to form the unitary gear assembly 28. This two-piece gear construction forms a practical manner of forming the appropriate plastic flow paths, but the gear assembly could be formed in other ways such as by casting.

Figure 9:
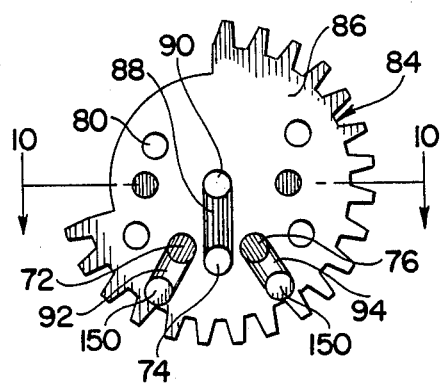
FIG. 9 is a rear elevational view of the forward half of the gear assembly showing the extrusion channels therein.

The second element or gear 84 is provided with a rear face 86 such as shown in FIG. 9 which includes a flow channel 88 connecting a central opening 90 with the middle of the three openings in the first gear 64, that is, opening 74. In addition, a pair of dump channels 92 and 94 respectively connect the openings 72 and 76 to the peripheral edge of the gear assembly 28 via dump openings 93 and 95 respectively. The cross-sectional extent of such dump openings roughly approximates that of the extrusion orifice through which the desired article is forced such that the extrusion pressures between the product path and the material being dumped is roughly equal. Such is desirable so that when the gear assembly 28 is switched back and forth between the first and second positions, the product flow pressure is not unduly changed which could cause undesirable changes in the density, shape and other article characteristics upon extrusion. The openings 93 and 95 face cut-out 53 such that resin from the extruder being dumped simply passes out the appropriate opening into the cut-out 53 and thence out of the head 18 to waste.

As best shown by reference to FIGS. 9 through 13, it should be clear that plastic resin from either one of the two extruders 1 or 2 will move from the base section 48 through the gear assembly 28 and thence to the forward section 51 of the head 18 through a central opening 100 provided therein and in which the die assembly 102 is mounted. Which resin is extruded into product through the die assembly and which resin is dumped from the gear assembly will, of course, depend on the position of the gear assembly at any given time.

Such die assembly 102 includes conventional portions but with modifications which will be referred to as the following description proceeds. The face of the forward section 51 of the extrusion head 18 is provided with a large central recess 104 and a contiguous countersunk recess 106. The forward outer section 108 of a die assembly is mounted in the larger recess 104 with an apertured plate 110 secured to the face 112 of the front section 51 via bolts 114. Adjustment is provided by conventional adjusting screws 116 radially positioned about the face 112 which provides for the proper positioning of the outer die portion 108 vis-a-vis a centrally disposed die mandrel 118. The mandrel 118 is further mounted in a holder 120 which in turn includes a plurality of openings 122 circularly disposed about the mandrel opening periphery 124 such that extrusion or resin coming from the opening 90 of the gear assembly 28 is diverted through the openings 122 and thence through the extrusion passage 126 formed between the mandrel 118 and the similarly shaped opening 128 in the outer die portion 108. The generally conical face 130 of the mandrel 118 is provided with a series of grooves 132 to, in effect, increase the laminar flow properties imparted to the molten resin as it passes through the passage 126 and thence to the die opening 132 where the resin is subsequently cooled and taken up in the intended manner.

Figure 10:
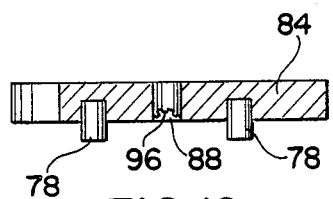
FIG. 10 is a cross-sectional view taken along the line 10—10 of FIG. 9.
Figure 11:
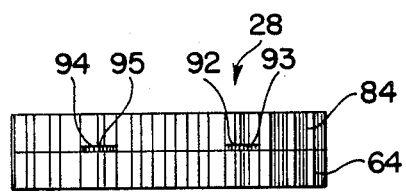
FIG. 11 is an edge elevational view of the gear assembly.
Figure 13:
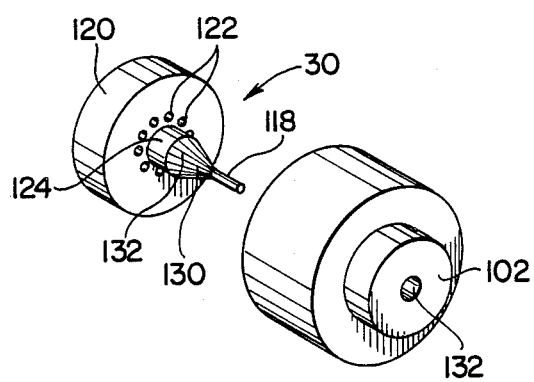
FIG. 13 is an exploded perspective view of the die assembly of the present invention.
Figure 12:
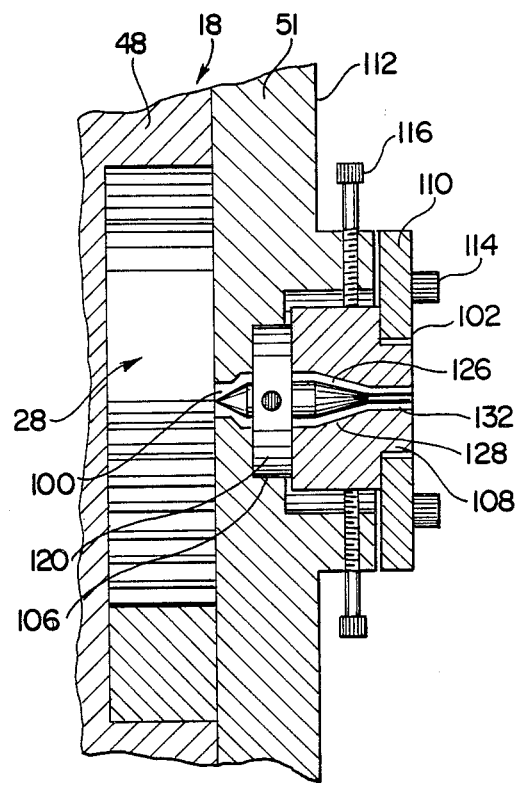
FIG. 12 is a cross-sectional view taken along the line 12—12 of FIG. 4.

In addition to the above specialized configurations to impart laminar flow to the extrusion mass, the channel 88 in the second gear 86 is also provided with a series of grooves 96 shown best in FIG. 10. It is particularly important that laminar flow rather than a more normal viscosity profile occur in the extrusion passages. In other words, a channeled melt flow is desired to reduce the time in which mixing of the two resins takes place upon switching extrusion positions. As the resins move from either of the extruders through the extrusion assembly 17, the flow of a first resin through the orifice 132 is quickly changed to the flow of the second resin without a gradual mixing of the resins from decidedly slower flowing resin adjacent the extrusion passage walls as would exist with a normal viscosity profile of melt flow in a round channel. The quick change from one resin to the other with channeled melt flow is the desired process operation of the above-described apparatus to form the article 10 in the intended manner. Thus if normal turbulent flow was permitted, the time or length distribution in the final article 10 would be increased, that is, the material being extruded as product would tend to mix with peripheral portions or the previously extruded material and thus take a longer time period to emerge as a pure material from the orifice 132. Other features which facilitate this overall result includes a streamlined die and mandrel to eliminate any dead spots where the material would tend to mix and therefore not transfer quickly, and by keeping the overall mixing sections of the two materials to a minimum, i.e., under two inches, keeps the chance of the two materials mixing to a minimum. Also, a quick smooth movement of the gear has been accomplished by using the brass bushings at all contact points.

It should thus be apparent that the overall concept of the invention is to provide constant extrusion from two extruders 1 and 2 to the common extrusion head 18. The extruder size is a variable and varies according to the tubing geometry or the material type being extruded. Each extruder is connected by a threaded adapter to the main head 18.

The gear assembly 28 has two positions. Thus in the first position as shown in FIGS. 6 and 7, product is being formed, that is, extruded from the orifice 132, by material coming from extruder 1 via path 1A and opening 62 while the material being fed from extruder 2 via path 2A and opening 61 is being dumped, that is, simply allowed to pass through opening 76 and channel 94 and ooze between the plates 64 and 86 and thence outwardly from the recess 53 to waste beneath the extruder head 18. Thus in the alternate position, as shown in FIG. 8, the gear assembly 28 has been rotated counterclockwise such that it abuts stop 58 such that the product extrusion path is from opening 61 via opening 74 and channel 88 into opening 90 and thence through the die assembly, and the flow from extruder 1 via path 1A and openings 62 is dumped via channel 92 through opening 76.

It can be important to control the dump or back pressure of the extrusion path not producing product such that the extrusion pressures of both paths are equal such as when the program calls for movement of the gear assembly to the alternate or second position such as shown in FIG. 8. Such pressure difference could undesirably cause momentary changes in the configuration, density, or appearance of the product being extruded.

Figure 14:
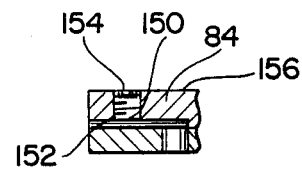
FIG. 14 is a cross-sectional view along the line 14—14 of FIG. 8.

Turning now to FIG. 14, the manner in which back pressure may be controlled by regulating, in effect, the size of the dump orifices 93 and 95 will be hereinafter described.

It will be thus apparent that a boss 150 is positioned in a bore 152 in the second gear 4. The bore 152 passes through the gear 4 and includes an allen or slotted head 154 opening in the upstream side of the gear face 156. In order to make the slotted head 154 accessible from the outside of the head 18 while the extrusion process is being carried out, a pair of bores 158 are provided through the front section 51 and terminate in openings 160 at the front face thereof. The bores 158 terminate and are respectively aligned with the bores 152 such that the bosses 150 may be adjusted inwardly or outwardly of the dump channels 92 and 94 so as to regulate the effective cross sectional thereof and thus the extrusion pressure therein. This can be done while the operation is running as with a wrench or screw driver so that the pressure of each of the dump paths can be adjusted to substantially equal that of the article extrusion path.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. The method of extrusion forming an article in the form of a continuous elongated strand wherein finite length portions of said strand form the article and the article has first and second terminal end portions formed of compatible first and second melt mixable plastics exhibiting differing physical properties and an intermediate connecting portion formed of a melt extrusion blending of the first and second plastics connecting the end portions, comprising, continually extruding both said first and second plastics from separate extrusion sources to an extrusion head having a downstream longitudinally directed common article extrusion path and separate upstream longitudinally directed first and second dump extrusion paths so as to direct said first plastic through said article extrusion path for subsequent cooling and processing to form said article while simultaneously laterally directing said second plastic through said second dump path to waste and thereafter intermittently and in timed sequence quickly redirecting the extrusion paths of said first and second plastics so as to longitudinally direct said second plastic through said article extrusion path and said first plastic laterally through said first dump path.

2. The method of claim 1, including maintaining the extrusion pressure in both said article extrusion path and the dump path being simultaneously utilized at a substantially equal level.

3. The method of claim 2, including adjusting the cross-sectional area of said dump paths while extruding to maintain the extrusion pressures in said dump paths to substantially the level of said article extrusion path.

4. The method of claim 1, including maintaining substantially laminar plastic flow in said article flow path regardless of which of said plastics is flowing therethrough.

5. The method of claim 1 wherein said first and second dump extrusion paths each comprising a first upstream longitudinally directed sector substantially parallel to said common article extrusion path and a second downstream laterally directed sector open to waste, said first sector of each said dump extrusion path and said common extrusion path comprising an overall longitudinally directed composite path through which said article is extruded.

6. The method of claim 4 wherein said extrusion plastic is directed from said first and second longitudinally directed dump extrusion paths laterally inwardly to said downstream longitudinally directed common article extrusion path while said second plastic is laterally outwardly directed to waste.

7. The method of claim 6 wherein laminar flow is maintained in said laterally inwardly directed path by means of separating said flow into a series of parallel paths.

8. Apparatus for forming an article in the form of a continuous elongated strand wherein finite length portions of said strand form the article and the article has first and second terminal end portions formed of compatible first and second melt mixable plastics exhibiting differing physical properties and an intermediate connecting portion formed of a melt extrusion blending of the first and second plastics connecting the end portions, comprising, a pair of extruders connected to a common extrusion head in turn having a downstream longitudinally directed common article extrusion path and separate upstream first and second dump extrusion paths, said first and second dump extrusion paths each comprising a first upstream longitudinally directed sector substantially parallel to said common article extrusion path and a second downstream laterally directed sector open to waste, said first sector of each said dump extrusion path and said common extrusion path comprising an overall longitudinally directed composite path through which said article is extruded, and rotational means in said head for quickly directing and redirecting said first and second plastics from said extruders sequentially from said article extrusion path to one said dump paths and vice versa.

9. The apparatus of claim 8, said rotational means being an element mounted for partial back and forth rotation in said head, said head in turn having a surface with a pair of openings in turn connected to said extruders and forming a portion of the initial flow paths of said extruders, said elements having a first upstream face mounted generally transverse to the initial flow paths of said two extruders and having three arcuately in line separated openings passing through said face, said face openings in turn respectively connected to portions of a first dump path, an article flow path and a second dump path, said rotational means adapted to move said element from one position wherein the respective surface opening of one extruder is aligned with the central face opening corresponding to the article extrusion path and the surface opening of the other extruder is aligned with one of the other openings corresponding to a dump path to a second position where the respective surface opening of the second extruder is aligned with the central face opening corresponding to the article extrusion path and the surface opening of the first extruder is aligned with a dump path opening.

10. The apparatus of claim 9, said element being a generally cylindrical gear, said gear being driven by a reciprocating rack tooth engaged with said gear.

11. The apparatus of claim 9, including means for adjusting the cross sectional extent of said dump paths.

12. The apparatus of claim 11, said adjusting means including a longitudinally movable section movable inwardly and outwardly of said dump flow paths to regulate the cross-sectional area and thus the pressure therein and means accessible from the outside of said head for moving said movable sections.

13. The apparatus of claim 12, said movable sections being threadable bosses having screw heads opening at an upstream face of said element.

14. The apparatus of claim 9, said element being of two-part connected construction.

15. The apparatus of claim 9, including programmed means for controlling the switching movement and dwell sequences of said element.

* * * * *